United States Patent [19]

Braun et al.

[11] Patent Number: 4,505,273
[45] Date of Patent: Mar. 19, 1985

[54] SURGICAL STAPLE

[75] Inventors: Karl Braun, Talheim; Jurgen Fetzer, Gerstetten-Dettingen, both of Fed. Rep. of Germany

[73] Assignee: Intermedicat GmbH, Emmenbrucke, Switzerland

[21] Appl. No.: 465,319

[22] Filed: Feb. 9, 1983

[30] Foreign Application Priority Data

Feb. 10, 1982 [DE] Fed. Rep. of Germany ....... 3204532

[51] Int. Cl.³ .................. A61B 17/08; A61B 17/04
[52] U.S. Cl. .................. 128/335; 128/334 R; 411/457; 411/481
[58] Field of Search ............ 128/335.5, 335, 334 R, 128/346, 325, 326; 227/19, 120; 411/457, 481, 483, 492, 493, 499

[56] References Cited

U.S. PATENT DOCUMENTS

| | | | |
|---|---|---|---|
| 3,120,230 | 2/1964 | Skold | 128/346 |
| 3,825,009 | 7/1974 | Williams | 128/334 R |
| 3,867,944 | 2/1975 | Samuels | 128/334 R |
| 4,256,251 | 3/1981 | Moshofsky | 227/120 |
| 4,391,401 | 7/1983 | Moshofsky | 227/19 |
| 4,396,139 | 8/1983 | Hall et al. | 227/19 |
| 4,399,810 | 8/1983 | Samuels et al. | 227/19 |

Primary Examiner—C. Fred Rosenbaum
Assistant Examiner—C. W. Shedd
Attorney, Agent, or Firm—Kenyon & Kenyon

[57] ABSTRACT

A surgical staple is disclosed comprising an arcuate central region which can be flattened by a stapling tool. Straight legs extend obliquely upwardly from the central region to which are connected downwardly extending side portions. The side portions are curved substantially in the form of an arc of a circle having a center at the center for the central region. When the central region is flattened, the side portions move about an arc of a circle so that automatic puncture channels are produced. Tearing of tissue is thereby prevented.

6 Claims, 6 Drawing Figures

SURGICAL STAPLE

BACKGROUND OF THE INVENTION

The present invention relates to a surgical staple for closing or suturing a wound or incision, particularly a surgical skin staple adapted to be implanted in or through the skin to suture an exterior wound or incision.

Surgical staples having a central portion and opposed side portions with points or cutting edges at their free ends or tips have been used for holding tissue at the edges of a wound or incision together until sufficient scar tissue forms to firmly connect the tissue so that the staple may be removed. A staple of the type disclosed in DE-PS No. 26 25 991 and U.S. Pat. No. 3,662,939 includes a straight central portion and straight side portions each forming an angle of 90° with the central portion. Such staples are deformed in a tool between a ram and an anvil in such a way that the ends of the side portions are bent around the anvil edges at an angle of 90°. One disadvantage in the use of such a staple occurs during implanting. Since the staple tips tear rather than stab through the tissue to be joined in the region adjacent the wound during deformation of the staple, a large traumatic laceration channel is produced by each of the two side portions. There is the additional disadvantage that during removal the staple is not bent back to its original form, but is deformed in the central portion into the shape of an arc so that the side portions are bent up at an angle. The angularly-bent side portions traverse an unfavorable path through the tissue and freshly widen and injure the tissue. This process entails considerable pain for the patient.

Another disadvantage of a staple of the type disclosed in the aforementioned documents is that it is normally not suitable for stacking in a magazine having an arcuate feed path. It is often desirable in surgical staplers to use a staple magazine which includes a curved section through which the staples are advanced. However, staples of the above-described type cannot be used in such a magazine because, due to the substantially straight central portion of the staples, exact guiding and simple spring-biased advancing of the staples through the curved section of the magazine is not possible.

OBJECTS AND SUMMARY OF THE INVENTION

It is an object of the present invention to provide a surgical staple, particularly a skin staple, which forms an automatic puncture channel upon being applied to a wound or incision so that tissue injury is reduced to the extent absolutely necessary.

It is another object of the present invention to provide a surgical staple, particularly a skin staple, which can be used in a staple magazine which includes one or more curved sections through which the staples are advanced.

The above and other objects are achieved according to the invention disclosed herein which provides a surgical staple having a central portion which includes an upwardly concave arcuate region and opposed side portions. The arcuate region faces or is curved in the direction of the side portions, i.e. the closed part or exterior of the arcuate region faces in the direction of the side portions. The arcuate central region is adapted to be flattened between the ram and anvil of a tool when closing, i.e. applying, the staple, thereby causing a substantially circular movement of the tips or ends of the side portions.

According to the invention, the tips of the inventive staple move along a circular path both during closing or implanting (stapling) and during removal (unstapling) of the staple. The center of the circular path is located to the open side of the arcuate region and preferably within the arcuate region of the central portion of the staple. The arcuate region is curved such that the side portions during closing follow the respective staple tip in the direction of movement so that the puncture channel is neither injured nor widened during implanting of the staple. Since the center of the circular path followed by the tips and the side portions lies to the open side of the arcuate region, it lies behind the anvil surface and deep seating of the staple in the tissue is obtained. The unfavorable so-called ladder effect is thereby minimized.

The inwardly bent central region of the staple of the invention provides several further advantages. It enables the force of the compression spring of a staple magazine to act on the planar center of gravity of stacked staples so that an additional slide is not necessary for the staple mechanism. In addition, a stack of the inventive staples can easily be advanced through one or more curved sections in a staple magazine.

According to a preferred embodiment of the invention, the arcuate central region of the staple extends along an arc of a circle of constant radius.

Preferably, a straight leg is disposed between the central arcuate region and each side portion of the staple. As a result, in the closed condition of the staple, its greatest width is in the pulling or closing direction of the stapled tissue edges. In addition, the staple does not pivot or turn in the tissue under tensile stress. During closing or forming of the staple, the legs are pivoted around the ends of the curved central region and in the closed conditon extend laterally spread apart and protrude into the interior of the tissue. The legs preferably are bent at an angle to the arcuate central region such that after the arcuate central region is flattened, the tips of the side portions abut against or are at least closely adjacent each other.

According to a preferred embodiment of the invention, the leg portions are curved, at least in sections, with a radius or radii of a curved section or sections preferably centered at the center of the arcuate central region. The center of the curved path followed by the side portions therefore coincides with the center of the curved central region. This configuration insures that at least the end or tip regions of the side portions follow a circular path during implanting of the staple and carry out a purely stabbing movement.

Preferably the side portions include a single curved section and the tangent to the center of the curved section extends at an angle of less than about 60° with respect to the respective straight leg.

The above and other objects, features, aspects and advantages of the invention will be more readily perceived from the following description of the preferred embodiments thereof when considered with the accompanying drawings and appended claims.

BRIEF DESCRIPTION OF THE DRAWINGS

The present invention is illustrated by way of example and not limitation in the figures of the accompanying drawings in which like numerals indicate similar parts and in which.

DESCRIPTION OF THE PREFERRED EMBODIMENTS

A preferred embodiment of the invention is illustrated and described in connection with a skin staple adapted to be applied to an exterior wound or incision across a layer of skin, although the invention is not limited to such surgical skin staples.

Figure 1:
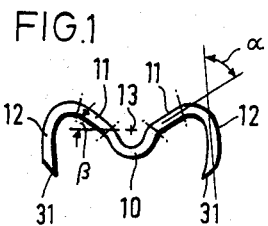
FIG. 1 is a side view of a staple according to the present invention.

The staple illustrated in FIG. 1, made of a deformable metal, comprises a central portion which includes a semicircular central region 10 and straight legs 11 projecting obliquely outwardly from the respective ends of the semicircular region at an angle $\beta$ of less than about 30° with respect to the diameter of the semicircular region which extends to the ends of the central region 10. Contiguous to each leg 11 is a side portion 12 which is arcuate and includes an outer section which extends approximately along an arc of a circle centered at the center 13 of the central region 10. The tips or ends 31 of the side portions 12 are formed as points or cutting edges. The tangent to the center of the arcuate part of side portion 12 extends at an angle $\gamma$ of less than about 60° with respect to the longitudinal axis of the respective straight leg 11. While the legs 11 relative to the diameter passing through the center 13 and the ends of the central portion 10 are directed obliquely upwardly and outwardly, the side portions 12 extend substantially vertically downwardly, their ends 31 being turned inwardly toward each other.

Figure 2:
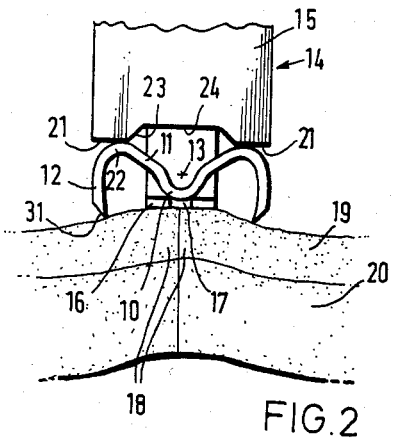
FIG. 2 is a side schematic view depicting the staple of FIG. 1 and the tip of a tool for implanting the staple positioned ready to implant the staple across an incision line.

FIG. 2 illustrates the disposition of the staple above the incision in just prior to implanting the staple. The staple is inserted in a tool 14 which comprises a ram or die 15 movable linearly relative to an anvil 16. Anvil 16 comprises a flat plate having a central slot 17 against the edges of which the outside of the central region 10 of the staple is set. The anvil 16 rests against the juxtaposed wound edges 18 of the skin layer 19. The subcutaneous tissue is designated 20. The ends 31 of the staple touch the upper skin layer 19.

Die 15 comprises two lateral end faces 21 which press against the arcuate knee regions 22 at the transition of the side portions 12 to the legs 11. Interposed between the end faces 21 is a trapezoidal-shaped recess having sides 23 directed inwardly and upwardly from the end faces at an angle of less than about 45°. The width of the base wall 24 of the recess corresponds to the width of the anvil 16 plus double the material thickness of the staple. The width of the anvil 16 in turn corresponds generally to the central region 10.

Figure 3:
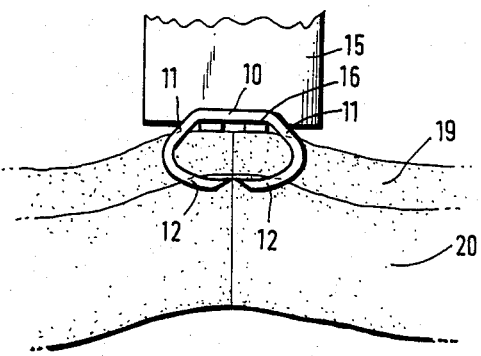
FIG. 3 is a side schematic view depicting the staple and the tool of FIG. 2 after the staple has been implanted.
Figure 4:
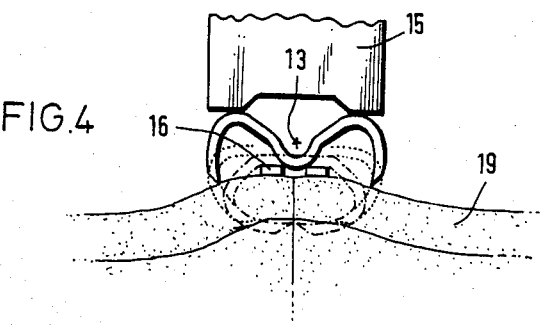
FIG. 4 is a side schematic view depicting the staple and tool of FIG. 2 as the staple is being implanted.

As depicted in FIG. 4, when die 15 is moved downwardly, the staple becomes deformed exclusively in the vicinity of the arcuate central region 10, which is flattened on the anvil 16 until the ends of the central region 10 are bent over the edges of the anvil. Finally, as depicted in FIG. 3, the sides 23 of the die 15 are positioned against the straight legs 11, which now point obliquely downwardly with the ends of the side portions 12 of the staple abutting against each other. During deformation of the staple as described above and depicted in FIG. 4, the side portions 12 move along an arc of a circle centered at 13. Both side portions thus follow circular puncturing movements into the skin layer 19 resulting in two automatic puncture channels without lacerations. Thereafter tool 14 is removed by retracting die 5 and then pulling anvil 16 out from under the central region 10.

Figure 5:
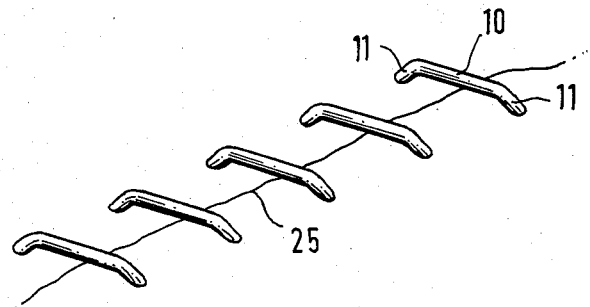
FIG. 5 is a perspective view of the stapled and closed wound.

FIG. 5 shows the closed wound. The wound edges are well conformed and the incision line 25 is slightly raised to compensate for shrinkage as the wound heals. As a consequence of the staple configuration and the manner in which it is closed, the staple is horizontally oriented, i.e. it lies flat on the skin surface. Because the legs 11 extend obliquely downwardly from the now straightened central region 10, a ladder impression on the wound region is prevented and it is possible to grip the staple in a simple manner with a staple remover. Staple portions 10 and 11, which protrude from the skin and can interfere when dressing the wound, are quite small.

Figure 6:
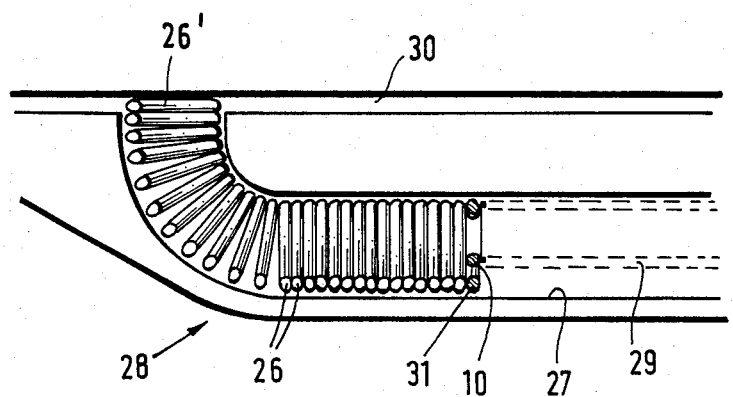
FIG. 6 is a side view of a curved stacking magazine in which the staples of FIG. 1 are advanced.

FIG. 6 shows numerous staples 26 disposed in the feed channel 27 of a staple magazine 28. Feed channel 27 contains a compression spring 29 which engages the rearwardmost staple in the vicinity of its curved central region 10 which is the approximate horizontal and vertical center of the staple, i.e. the planar center of gravity of the staple. Hence spring 29 acts on the center of the staples so that the magazine feed channel 27 can be curved and the tips and respective side portions 31 of the staple can point outwardly in the curved section. The magazine feed channel 27 opens into a transversely-extending staple channel. The forwardmost staple 26' as advanced by the spring enters the transversely-extending guide channel 30, where it can be engaged and removed by a slide (not shown) and supplied to the tool 14.

Certain changes and modifications of the embodiments of the invention disclosed herein will be readily apparent to those skilled in the art. It is the applicants' intention to cover by their claims all those changes and modifications which could be made to the embodiments of the invention herein chosen for the purpose of disclosure without departing from the spirit and scope of the invention. The various directions in the claims are with respect to the drawings and not necessarily to the staple as it is used.

What is claimed is:

1. A surgical staple for closing wound edges comprising a central portion and opposed side portions, the central portion including an upwardly concave arcuate region having a substantially constant radius of curvature adapted to be flattened by a stapling tool such that a substantially circular substantially downward movement of the side portions is produced, each side portion including an end section which extends approximately along an arc having a radius of curvature centered at substantially the center for the arcuate central region, and having a free end configured so as to facilitate cutting or puncturing of skin or tissue.

2. The surgical staple according to claim 1 further comprising a straight leg having a longitudinal axis, disposed between the arcuate central region and each side portion.

3. The surgical staple according to claim 2 wherein the legs are directed obliquely upwardly and outwardly, and the side portions extend substantially vertically downwardly.

4. The surgical staple according to claim 3 wherein the tangent to the center of a side portion section extends at an angle of less than about 60° to the longitudinal axis of the associated straight leg.

5. The surgical staple according to claim 2 wherein the tangent to the center of said side portion section extends at an angle of less than about 60° to the longitudinal axis of the straight leg.

6. The surgical staple according to claim 1 wherein a point on the curved arcuate region lies substantially in the centroid of the staple.

* * * * *

UNITED STATES PATENT AND TRADEMARK OFFICE
CERTIFICATE OF CORRECTION

PATENT NO. : 4,505,273

DATED : March 19, 1985

INVENTOR(S) : Braun, et al.

It is certified that error appears in the above-identified patent and that said Letters Patent is hereby corrected as shown below:

Column 4, line 13, the reference numeral "5" should read -- 15 --.

Signed and Sealed this

Sixteenth Day of July 1985

[SEAL]

Attest:

DONALD J. QUIGG

Attesting Officer

Acting Commissioner of Patents and Trademarks